US010220220B2

(12) United States Patent
Solehmainen

(10) Patent No.: US 10,220,220 B2
(45) Date of Patent: Mar. 5, 2019

(54) POSITION-FINDING APPARATUS

(71) Applicant: Nexstim Oy, Helsinki (FI)

(72) Inventor: Kai Solehmainen, Helsinki (FI)

(73) Assignee: Nexstim Oyj, Helsinki (FI)

( * ) Notice: Subject to any disclaimer, the term of this patent is extended or adjusted under 35 U.S.C. 154(b) by 346 days.

(21) Appl. No.: 14/740,299

(22) Filed: Jun. 16, 2015

(65) Prior Publication Data

US 2016/0001092 A1    Jan. 7, 2016

(30) Foreign Application Priority Data

Jul. 2, 2014    (FI) .................................... 20145644

(51) Int. Cl.
*A61N 2/02*      (2006.01)
*A61N 2/00*      (2006.01)
*A61B 34/20*     (2016.01)
*A61B 34/00*     (2016.01)

(52) U.S. Cl.
CPC ............. *A61N 2/02* (2013.01); *A61N 2/006* (2013.01); *A61B 34/20* (2016.02); *A61B 34/25* (2016.02); *A61B 2034/2051* (2016.02); *A61B 2034/2055* (2016.02); *A61B 2034/2063* (2016.02)

(58) Field of Classification Search
CPC .......... A61N 2/02; A61N 2/006; A61B 34/20; A61B 5/0042; A61B 5/7425
See application file for complete search history.

(56) References Cited

U.S. PATENT DOCUMENTS

| 2003/0004392 A1 | 1/2003 | Tanner et al. |
| 2003/0050527 A1 | 3/2003 | Fox et al. |
| 2008/0262338 A1 | 10/2008 | Paitel et al. |
| 2010/0210939 A1 | 8/2010 | Hartmann et al. |
| 2013/0178693 A1 | 7/2013 | Neuvonen et al. |
| 2014/0058189 A1* | 2/2014 | Stubbeman ............ A61N 2/002 600/13 |

FOREIGN PATENT DOCUMENTS

| CN | 101517618 A | 8/2009 |
| EP | 2703043 A1 | 3/2014 |

(Continued)

OTHER PUBLICATIONS

Kantelhardt et al: Robot-assisted image-guided transcranial magnetic stimulation for somatotopic mapping of the motor cortex: a clinical pilot study. Acta Neurochirurgica. Feb. 2010, vol. 152, Edition N2, pp. 333-343.

*Primary Examiner* — Christine H Matthews
(74) *Attorney, Agent, or Firm* — Seppo Laine Oy

(57) ABSTRACT

According to an example embodiment of the present invention, there is provided an apparatus comprising at least one receiver configured to receive signals relating to a position of a device relative to a head, at least one processing core configured to determine, at least in part based on the received signals, the position of the device relative to the head, to compare the position of the device relative to the head to information concerning a position corresponding to a maximal induced electric field, and to cause signals to be transmitted, and wherein the transmitted signals are configured to cause a display to indicate a deviation of the position of the device from the position corresponding to the maximal induced electric field.

19 Claims, 8 Drawing Sheets

(56) References Cited

FOREIGN PATENT DOCUMENTS

| | | |
|---|---|---|
| JP | 2012529947 A | 11/2012 |
| RU | 2373971 C2 | 11/2009 |
| WO | WO03084607 A1 | 10/2003 |
| WO | WO2008031847 A1 | 3/2008 |
| WO | WO2008031849 A2 | 3/2008 |
| WO | WO 2008133831 A2 | 11/2008 |
| WO | WO2010049575 A1 | 5/2010 |
| WO | WO 2010147064 A1 | 12/2010 |
| WO | WO 2011089606 A1 | 7/2011 |
| WO | WO2012059917 A1 | 5/2012 |
| WO | WO 2012147927 A | 11/2012 |
| WO | WO2013049345 A2 | 4/2013 |

\* cited by examiner

POSITION-FINDING APPARATUS

FIELD OF INVENTION

The present invention relates to positioning, fixing and/or moving devices with respect to person's head.

BACKGROUND OF INVENTION

Performing precision operations with instruments requires that the instruments are accurately positioned with respect to whatever the operations are being performed on. Transcranial magnetic stimulation, TMS, for example, is used to magnetically stimulate a small area inside a person's brain which requires that a magnetic coil used be positioned accurately, for shorter or longer periods of time, along the outside of the person's head. Similarly, for example, radiation therapy greatly benefits from aiming radiation patterns accurately at malignant cells to avoid damaging healthy tissue.

Using TMS as an example, a patient may be instructed to maintain his head immobile while a stimulating coil is moved along the outer surface of his head. If the coil is held accurately and reliably at the correct location, the stimulating effect can be aimed at a desired location inside the brain. On the other hand if the coil is inaccurately placed or accidentally moves, results of TMS are expected to be adversely affected.

TMS may be used, for example, to locate a position representing a certain muscle for defining a person's motor threshold position, to facilitate rehabilitation following a stroke or to treat depression, for example. Radiation therapy may be used to kill malignant cells. Using a manual placement technique, a treatment position on the patient's head or a position used to find a treatment position, such as the patient's motor threshold position, MTP, may be determined by moving a TMS coil near a predicted area determined by patient anatomical landmarks until the desired motor response is achieved.

US2009227830 describes an apparatus for positioning a medical instrument, such as a TMS coil, with respect to a patient.

SUMMARY OF THE INVENTION

According to a first aspect of the present invention, there is provided an apparatus comprising at least one receiver configured to receive signals relating to a position of a device relative to a head, at least one processing core configured to determine, at least in part based on the received signals, the position of the device relative to the head, to compare the position of the device relative to the head to information concerning a position corresponding to a maximal induced electric field, and to cause signals to be transmitted, and wherein the transmitted signals are configured to cause a display to indicate a deviation of the position of the device from the position corresponding to the maximal induced electric field.

Various embodiments of the first aspect may comprise at least one feature from the following bulleted list:
- the transmitted signals are configured to cause the display to indicate the deviation in terms of at least one of pitch, roll, yaw, rotation and distance
- the transmitted signals are configured to cause the display to indicate the deviation in terms of at least two of pitch, roll, yaw, rotation and distance
- the transmitted signals are configured to cause the display to indicate the deviation in terms of at least three of pitch, roll, yaw, rotation and distance
- the transmitted signals are configured to cause the display to indicate the deviation in terms pitch, roll, yaw, rotation and distance
- the apparatus is configured to cause the display to display a signal responsive to a determination that the device is at the position corresponding to the maximal induced electric field
- the apparatus is configured to trigger the device responsive to a determination that the device is at the position corresponding to the maximal induced electric field
- the at least one receiver is further configured to receive, from the device, at least one signal indicating whether the device is ready for use
- the apparatus comprises the device, the device comprising a transcranial magnetic stimulation device
- the deviation is such that moving the device to eliminate the deviation does not affect a location inside the head where the induced electric field is maximized
- the position corresponding to the maximal induced electric field comprises a position corresponding to the maximal induced electric field at a shown location
- the position corresponding to the maximal induced electric field comprises a position corresponding to the maximal induced electric field at a specific location.

According to a second aspect of the present invention, there is provided a method comprising receiving signals relating to a position of a device relative to a head, determining, at least in part based on the received signals, the position of the device relative to the head, comparing the position of the device relative to the head to information concerning a position corresponding to a maximal induced electric field, and causing signals to be transmitted, wherein the transmitted signals are configured to cause a display to indicate a deviation of the position of the device from the position corresponding to the maximal induced electric field.

Various embodiments of the second aspect may comprise at least one feature corresponding to a feature from the preceding bulleted list laid out in connection with the first aspect.

According to a third aspect of the present invention, there is provided An apparatus comprising means for receiving signals relating to a position of a device relative to a head, means for determining, at least in part based on the received signals, the position of the device relative to the head, means for comparing the position of the device relative to the head to information concerning a position corresponding to a maximal induced electric field, and means for causing signals to be transmitted, wherein the transmitted signals are configured to cause a display to indicate a deviation of the position of the device from the position corresponding to the maximal induced electric field.

According to a fourth aspect of the present invention, there is provided a non-transitory computer readable medium having stored thereon a set of computer readable instructions for causing a processor to display a list of items on an electronic device comprising the computer implemented steps of receiving signals relating to a position of a device relative to a head, determining, at least in part based on the received signals, the position of the device relative to the head, comparing the position of the device relative to the head to information concerning a position corresponding to a maximal induced electric field, and causing signals to be transmitted, wherein the transmitted signals are configured to cause a display to indicate a deviation of the position of the device from the position corresponding to the maximal induced electric field.

INDUSTRIAL APPLICABILITY

At least some embodiments of the present invention find industrial applicability in facilitating interactions between devices and human or non-human brains. For example, TMS device positioning may be improved in terms of time needed and/or accuracy attained to increase a strength of an induced electric field. At least some embodiments of the present invention provide the effect that interaction with a smaller brain area is enabled since a smaller electric field strength may be used, since positioning is more accurate.

DETAILED DESCRIPTION OF EXAMPLE EMBODIMENTS

Figure 1:
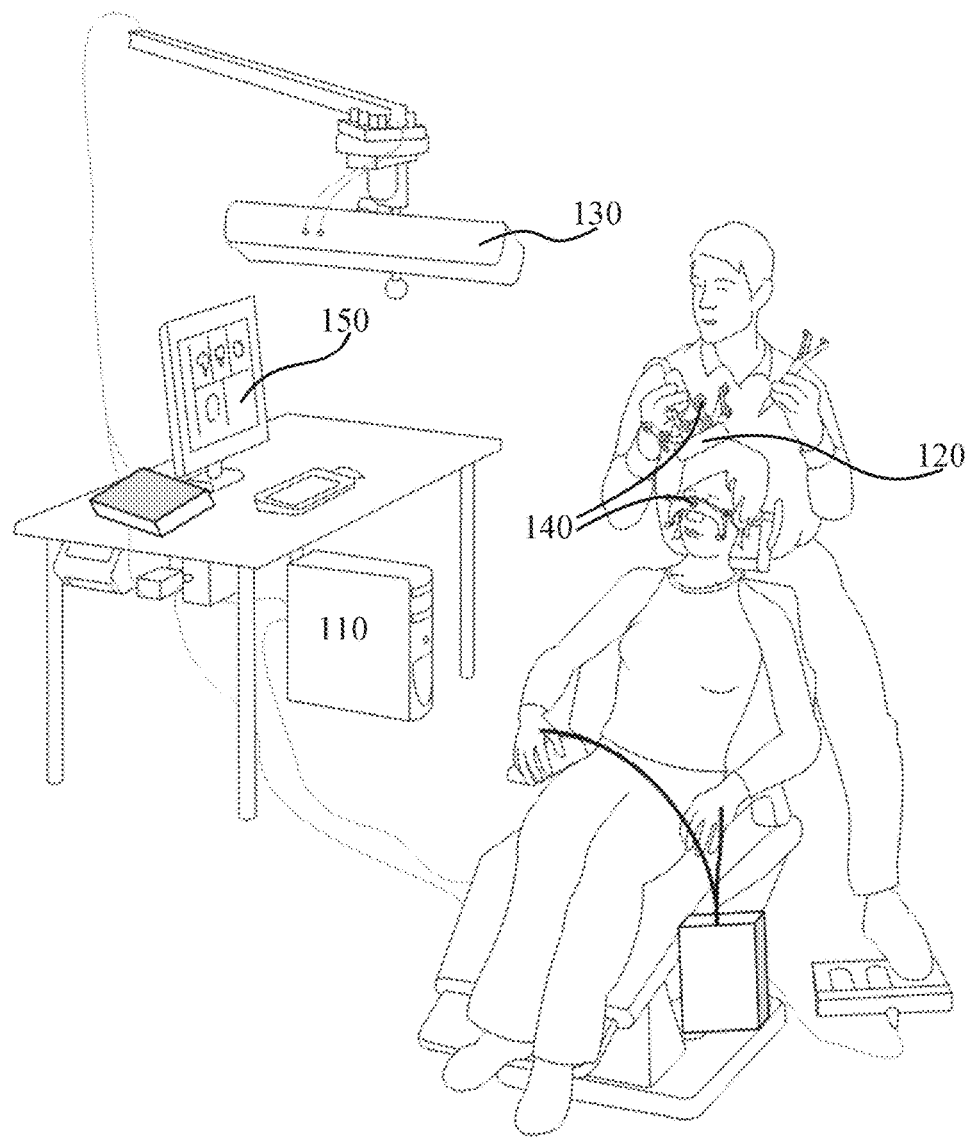
FIG. 1 illustrates an example system in accordance with at least some embodiments of the invention.

FIG. 1 illustrates an example system in accordance with at least some embodiments of the invention. The example of FIG. 1 may relate to a TMS system suitable for investigating anatomical features of a person's brain using electromagnetic fields, or treating the brain, for example. Illustrated is a chair, which may comprise a reclining treatment chair suitable for TMS or targeted radiation therapy, for example. On the chair is disposed a headrest, which may be contoured to assist a person sitting in chair in maintaining his head immobile. To such effect, the headrest may be at least in part comprised of a material that accepts and retains a shape of the back of a person's head, so the head can more easily be maintained stationary with respect to the chair.

An operator may place a device 120, such as for example a TMS coil, next to a person's head by hand and search for specific areas of the brain by monitoring for reactions responsive to magnetic stimuli generated by the coil. Holding a coil by hand for any period of time may tire the operator's hand even in case the coil is lightweight. When tired the operator becomes less capable of precisely holding the coil in place and the results of TMS may be affected. Also in case a break is needed during a TMS session, continuing may be difficult in case the exact place where the session was interrupted is not immediately findable. Maximizing a magnitude of an induced electric field in a specific direction may require for the coil to be placed in a specific orientation, which may be difficult for the operator to accomplish intuitively. The specific direction of the induced electric field may correspond to an orientation of neural pathways in the brain.

Accuracy requirements in TMS or radiation therapy may vary depending on the application. TMS may require an accuracy of at least 2 millimeters or 2 degrees, for example. An accuracy requirement of at least 2 millimeters may mean that a measurement needs to be capable of determining a position of device 120 with a measurement error of at most 2 millimeters. Alternatively, an accuracy requirement of 2 millimeters may mean that a location in a brain needs to be determined such that an error in the location in the brain is at most 2 millimeters. Accuracy requirements of radiation therapy may be substantially similar to that of TMS, as even larger tumours have edges that may be in direct contact with healthy tissue.

Device 120 may be operable to emit particulate beams or electromagnetic fields to the head of a person sitting in the chair. Device 120 may comprise a TMS coil, wherein the coil may be enabled to generate an electromagnetic field extending to a distance from the coil, to inside the head. A TMS coil may be a wound coil device including a casing and contained in the casing coil windings of an electrically conductive material. A TMS system may comprise a computerized electromechanical instrument that produces and delivers brief duration rapidly alternating, or pulsed, magnetic fields to induce electric currents directed at localized regions of the cortex. Device 120 may be powered by electric cabling, which may be connected to electric power and/or control devices. A TMS coil may be constructed to generate a magnetic field of known shape, the shape being determined at least in part by an arrangement of conductive material inside the casing of device 120.

A time-varying magnetic field induces an electric field. An electric field in turn may cause an electric current. A TMS coil configured to generate a magnetic pulse inside, or on the surface of, a brain thereby induces an electric field which likewise is disposed inside, or on the surface of, the brain. The strength of the electric field is dependent on the position of the coil. For example, once the coil is moved to a place where the electric field is induced in the correct place, the strength of the induced electric field in that place may depend on the position of the coil, position in this regard comprising aspects of at least one of pitch, roll, yaw, rotation and distance.

In the system illustrated in FIG. 1, an operator may use a display 150 to guide device 120 to a correct place and/or orientation for interacting with a treatment area, and/or to adjust a position of device 120 for maximizing a strength of an induced electric field. In this document, place combined with orientation may be referred to as a position. Device 120 and/or the head may be furnished with homing aids 140, which may comprise visual, magnetic, ultrasound or radio homing aids, for example. Visual homing aids may comprise coloured items attached to device 120 and/or the head, as illustrated in FIG. 1, or alternatively or additionally radio emitters or reflectors attached to device 120 and/or the head. Scanner 130 may comprise an apparatus enabled to determine relative positions of device 120 and the head. In embodiments where the homing aids are visual, for example white or reflective patches or balls, scanner 130 may comprise a video camera, for example a stereoscopic video camera or a normal two-dimensional video camera, enabled to determine the relative position of device 120 in terms of the head. In embodiments where homing aids are based on radio waves, scanner 130 may be a radio receiver, for example a radio receiver capable of determining at least one of a direction and distance of a transmission from the homing aids.

A computational algorithm may be used to determine the relative position of device 120 with respect to the head. Such an algorithm may rely at least in part on knowledge of physical dimensions of homing aids 140, so that when scanner 130 perceives the homing aids at an angle, the angle may be determined using information from scanner 130 and the knowledge of the physical dimensions of homing aids 140.

For a given location in or on the brain, device 120 may be able to cause an electric field to be induced therein from a plurality of different positions, or orientations. For example, without moving device 120 along the surface of the head, the strength of the induced electric field in the location may be modified by rotating device 120 about an axis that is perpendicular to the surface of the head at a place where device 120 touches the head. Likewise modifying pitch, roll, yaw and/or slightly moving device 120 along the surface of the head may modify the induced electric field strength without changing the place where the electric field is induced in or on the brain.

When treating a patient with device 120, for example by administering TMS, the patient may react to stimuli provided by device 120. For example pulses provided to a motor area of the cortex may cause slight twitching in a finger or wrist. This way, a treatment area may be identified. Anatomical features of a brain may additionally or alternatively be used in identifying a treatment area. For example, a dorsolateral prefrontal cortex, DLPFC, may be relevant in treating major depressive disorder. When a treatment area is identified, a computer 110 may be instructed to register the relative position of device 120 with respect to the head in a memory comprised in computer 110. More than one treatment area per head may be registered in computer 110. Computer 110 may store the at least one treatment area registered in terms of the relative positions of device 120 and the head, as determined from information received in computer 110 from scanner 130. Computer 110 may be configured to store, for each treatment area, orientations of device 120 and the head. In general computer 110 may store either the relative position of device 120 with respect to the head, or information relating to this relative position that allows the relative position to be unambiguously reconstructed. In this sense, the exact format of information stored in computer 110 should not be seen as limiting the scope of the present invention.

On subsequent treatment sessions, locating the treatment area or treatment areas presents a challenge as the area may be small, the operator may be a different person and the treated person may recline in the chair, bed or other receptacle used, in a slightly different way. In systems in accordance with at least some embodiments of the present invention, computer 110 is configured to cause display 150 to present indications aiding the operator to find the treatment area or treatment areas and/or to maximize a strength of an induced electric field.

The head may be furnished with homing aid 140, so computer 110 may receive homing information via scanner 130. Homing aid 140 may be attached to a section of the head that is repeatedly findable and usable, and relatively constant relative to the brain inside the head. For example, a point between the eyebrows may be relatively constant and immediately proximate to the skull. Alternatively or additionally, homing aid 140 attached to the head may be employed at least in part at the crux of helix. In some embodiments, the head may be furnished with a device resembling eyeglasses, the device resembling eyeglasses being furnished with said homing aids or constituting said homing aids itself.

In addition to locating the treatment area in primary and subsequent treatment sessions, indications may be presented to aid the operator to manoeuvre device 120 to an optimal position for providing a stronger, or maximal, electric field to a specific location. For example, upon placing device 120 so as to interact with the specific location, indications may be provided to aid the operator in changing the position, or orientation, of device 120 so as to increase the induced electric field strength in the specific location, without changing the location where the electric field is induced.

On any subsequent session, as homing aids 140 may be in same, or similar, locations with respect to device 120 and the head. In some embodiments, homing aids 140 need not be in exactly the same position, as the change in position of homing aids 140 may be calibrated by providing to computer 110 information on a deviation between a current position of homing aids 140 and the section of the head that is repeatedly findable and usable.

Computer 110 may be configured to cause display 150 to present the operator with indications concerning a deviation of the relative position between device 120 and the head from a relative position between device 120 and the head position corresponding to a maximal induced electric field. Computer 110 may be configured to calculate, or simulate, strengths of induced electric field at a specific location based at least in part on a model of a head that comprises a plurality of structures and/or layers, with different structures and/or layers having different electrical conductivity. The structures and/or layers may have different thicknesses and/or shapes. In various embodiments of the invention, the number of structures and/or layers computer 130 uses may vary. For example, a skull structure, comprised of bone, may have a first electrical conductivity, a liquid layer under the skull may have a second electrical conductivity and a brain matter structure, under the liquid layer may have a third electrical conductivity. Computer 110 may be configured to provide, via display 150, indicators to the operator in terms of degrees of freedom of device 120. In some embodiments, each of the provided indicators relates to one and only one degree of freedom of device 120.

For example, a first indicator may relate to a deviation from the desired position in terms of rotation of device 120 around an axis perpendicular to the surface of the head. This rotation may be referred to as yaw. Responsive to the first indicator, the operator may rotate device 120 until the first indicator no longer indicates a deviation in terms of the degree of freedom the first indicator is associated with. Yaw may be important since a magnetic field produced by a TMS coil, for example, may have a specific shape and direction. In order to interact with the specific location successfully, the electric field induced by the magnetic field may need to be aligned with neural pathways in the specific location. A first indicator may take the form of a toroid displayed about an origin on display 150, for example, with an indicated area on the toroid signifying a direction in which device 120 needs to be rotated to remove the deviation. Another example of a possible first indicator is an arrow displayed on a clock face indicating the extent and direction, or at least the direction, of rotation needed to render device 120 in the desired position in terms of yaw.

For example, a second indicator may relate to a translation of device 120 along the axis perpendicular to the surface of the head. Responsive to the second indicator, the operator may move device 120 until the second indicator no longer indicates a deviation in terms of the degree of freedom the second indicator is associated with. For example, this movement may relate to lifting device 120 from the surface of the head, or pressing device 120 closer to the surface of the head. A second indicator may take the form of an arrow pointing in a direction of movement needed to remove the deviation, for example.

For example, third and fourth indicators may relate to translation of device 120 along the surface of the head. Responsive to the third and fourth indicators, the operator may move device 120 along the surface of the head until the third and fourth indicators no longer indicate a deviation in terms of the degrees of freedom the third and fourth indicator are associated with. The third and fourth indicators may take the form of arrows displayed on display 150, indicating the direction or directions where device 120 needs to be moved to remove the deviation in terms of these translational degrees of freedom.

For example, a fifth indicator may relate to a pitch angle of device 120 along the surface of the head. Responsive to the fifth indicator, the operator may rotate device 120 until the fifth indicator no longer indicates a deviation in terms of the pitch of device 120. The fifth indicator may take the form of a curved arrow, for example, displayed on display 150 and indicating a direction where device 120 needs to be tilted to remove the deviation.

A sixth indicator may relate to a second pitch angle, ninety degrees deviated from the pitch angle associated with the fifth indicator. The second pitch angle may be referred to as a roll. The sixth indicator may take the form of a curved arrow, for example, displayed on display 150 and indicating a direction where device 120 needs to be tilted to remove the deviation Overall, using the indicators given, an operator may first, for example, move device 120 to a correct place on the head responsive to the indicators that relate to translational degrees of freedom, and once the translational indicators indicate device 120 is in the correct place, the operator may rotate device 120, using indicators that relate to rotational degrees of freedom, until the rotational indicators indicate device 120 is in a correct orientation to produce a maximal electric field strength in the specific location.

By maximal electric field strength it is herein meant an electric field strength that is close enough to a maximal strength, that a difference between the actual and maximal electric field strength is immaterial to the application, such as for example TMS.

The first, second, third, fourth, fifth and/or sixth indicators may be displayed on display 150 with an image of a head to make the indicators easier to comprehend. An origin may be displayed, which may be arranged by computer 110 to co-move along the image of the head as device 120 moves along the head of the person being treated. The origin may be displayed on the image of the head on display 150 at the same, or similar, location as the place on the real head where device 120 is disposed, to help the operator orient with the indicators. The indicators may be displayed about the origin.

Once device 120 no longer deviates from the correct position translationally and/or rotationally, computer 110 may be configured to cause an "all-clear" signal to be displayed on display 150, responsive to which the operator may trigger device 120. The "all-clear" signal thus essentially corresponds to a signal indicating device 120 is well placed to induce a high electric field in the specific location in or on the brain. Triggering device 120 may comprise, for example, causing device 120 to emit at least one magnetic pulse where device 120 comprises a TMS device. Triggering of device 120 may comprise, for example, causing device 120 to emit radiation where device 120 comprises a radiation-therapy device.

Computer 110 may be configured to, responsive to a determination made in computer 110 that device 120 is in the correct position, trigger device 120 without intervention from the operator. An advantage of this is that a pulse may be administered to the specific location even in case the operator manages to secure the correct position for device 120 only fleetingly. Computer 110 may be configured to trigger device 120 responsive to determining that an electric field strength device 120 would induce in the specific location exceeds a threshold strength. An example threshold strength is 110 V/m.

In general where more than one change in position is indicated, the sum of the indicated changes in position may be such that the specific location where the electric field is induced does not change if the indicated changes in position are all made. Initially when the operator moves the device along the surface of the head, computer 110 may display on display 150 an interaction point indicating where in or on the brain the electric field would be induced, should the device be triggered. Once the operator is satisfied the interaction point is where he wants it to be, he may consult the indication(s) of deviation to maximize the induced electric field in the selected interaction point. While the sum of the indicated changes in position may keep the interaction point unchanged, correcting the deviations one by one may result in movements of device 120 that slightly move the interaction point. For example, where two changes in position are indicated, correcting only one of them may move the interaction point slightly.

In some embodiments, device 120 or computer 110 comprises a user interface element, such as a button or voice command receiver, that the operator may use to lock the interaction point in place in computer 110. Subsequently, the indicated changes in position will be presented in terms of allowing the operator to position device 120 so that a maximal electric field can be induced in the selected, locked, interaction point. When the interaction point is locked, the operator can correct the deviations one by one, without computer 110 re-calculating a new optimal position for device 120 if the interaction point moves as a result of correcting only part of the indicated deviations. This also provides the benefit that in case the operator accidentally moves device 120 while correcting the deviations, he is enabled to return device 120 to the correct location using the indicated deviations, since the indicated deviations are dynamically updated to guide device 120 to the optimal position, including orientation, to deliver a high electric field to the locked interaction point.

Computer 110 may be configured to receive, from device 120, a signal informing that device 120 is ready for use. Computer 110 may display an indication of readiness of device 120 in display 150. Such a signal of readiness may be based on the signal informing computer 110 that device 120 is ready.

Figure 2:
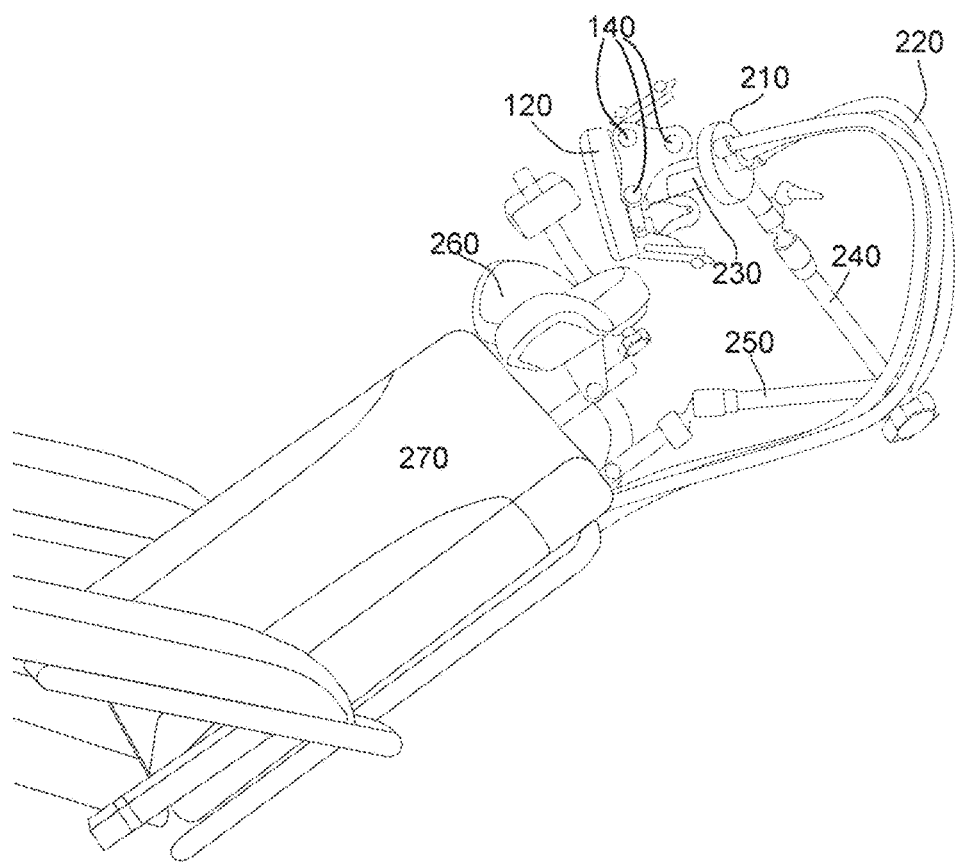
FIG. 2 illustrates an example apparatus in accordance with at least some embodiments of the invention.

FIG. 2 illustrates an example apparatus in accordance with at least some embodiments of the invention. Illustrated is a reclining chair 270 suitable for receiving a person for treatment of at least one treatment area inside the head. The chair according the illustrated example comprises a headrest 260, which may comprise a suitably form-accepting material to accept and hold steady the head. Reference numerals 120 and 140 denote similar structure as in FIG. 1, namely device 120 may be capable of administering treatments or interventions to treatment areas inside the head, and homing aids 140 are rigidly attachable to device 120 to assist in positioning of device 120 relative to the head. Device 120 may be attached to chair 270 by means of arms 230, 240 and 250. Coupling 210 may provide an adjustable coupling of arm 230 to arm 240. Cabling 220 may provide electric power, control signalling and/or cooling to device 120.

Figure 3:
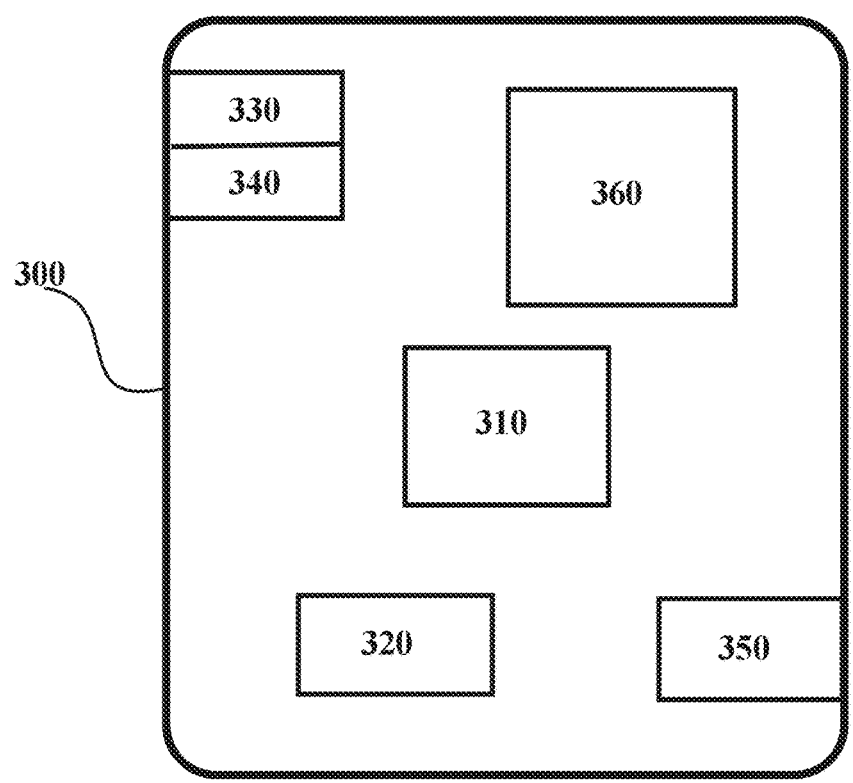
FIG. 3 illustrates an example apparatus capable of supporting at least some embodiments of the present invention.

FIG. 3 illustrates an example apparatus capable of supporting at least some embodiments of the present invention. Illustrated is device 300, which may comprise, for example, a computer device such as computer 110 of FIG. 1. Comprised in device 300 is processor 310, which may comprise, for example, a single- or multi-core processor wherein a single-core processor comprises one processing core and a multi-core processor comprises more than one processing core. Processor 310 may comprise a Qualcomm Snapdragon 800 processor, for example. Processor 310 may comprise more than one processor. A processing core may comprise, for example, a Cortex-A8 processing core manufactured by Intel Corporation or a Brisbane processing core produced by Advanced Micro Devices Corporation. Processor 310 may comprise at least one application-specific integrated circuit, ASIC. Processor 310 may comprise at least one field-programmable gate array, FPGA. The aforementioned processor types are non-limiting examples, alternatively an Intel i7 processor, or another suitable type of processor, may be employed.

Device 300 may comprise memory 320. Memory 320 may comprise random-access memory and/or permanent memory. Memory 320 may comprise at least one RAM chip. Memory 320 may comprise magnetic, optical and/or holographic memory. Memory 320 may be at least in part accessible to processor 310. Memory 320 may be means for storing information. Memory 320 may comprise computer instructions that processor 310 is configured to execute. When computer instructions configured to cause processor 310 to perform certain actions are stored in memory 320, and device 300 overall is configured to run under the direction of processor 310 using computer instructions from memory 320, processor 310 and/or its at least one processing core may be considered to be configured to perform said certain actions.

Device 300 may comprise a transmitter 330. Device 300 may comprise a receiver 340. Transmitter 330 and receiver 340 may be configured to transmit and receive, respectively, information in accordance with systems, for example transmitter 330 may transmit information to a monitor for display to a user, and/or receiver 340 may receive input information concerning a location and/or orientation of a further device.

Device 300 may comprise a near-field communication, NFC, transceiver 350. NFC transceiver 350 may support at least one NFC technology, such as NFC, Bluetooth, Wibree or similar technologies.

Device 300 may comprise user interface, UI, 360. UI 360 may comprise at least one of a display, a keyboard and a touchscreen. A user may be able to operate device 300 via UI 360, for example to start or terminate execution of programs.

Processor 310 may be furnished with a transmitter arranged to output information from processor 310, via electric leads internal to device 300, to other devices comprised in device 300. Such a transmitter may comprise a serial bus transmitter arranged to, for example, output information via at least one electric lead to memory 320 for storage therein. Alternatively to a serial bus, the transmitter may comprise a parallel bus transmitter. Likewise processor 310 may comprise a receiver arranged to receive information in processor 310, via electrical leads internal to device 300, from other devices comprised in device 300. Such a receiver may comprise a serial bus receiver arranged to, for example, receive information via at least one electric lead from receiver 340 for processing in processor 310. Alternatively to a serial bus, the receiver may comprise a parallel bus receiver.

Device 300 may comprise further devices not illustrated in FIG. 3. For example, where device 300 comprises a computer device, it may comprise at least one clock or auxiliary power unit, APU to provide battery power in case of mains power failure.

Processor 310, memory 320, transmitter 330, receiver 340, NFC transceiver 350 and/or UI 360 may be interconnected by electric leads internal to device 300 in a multitude of different ways. For example, each of the aforementioned devices may be separately connected to a master bus internal to device 300, to allow for the devices to exchange information. However, as the skilled person will appreciate, this is only one example and depending on the embodiment various ways of interconnecting at least two of the aforementioned devices may be selected without departing from the scope of the present invention. In some embodiments, computer 110, device 120, scanner 130 and/or display 150 are comprised in one physical entity.

Figure 4:
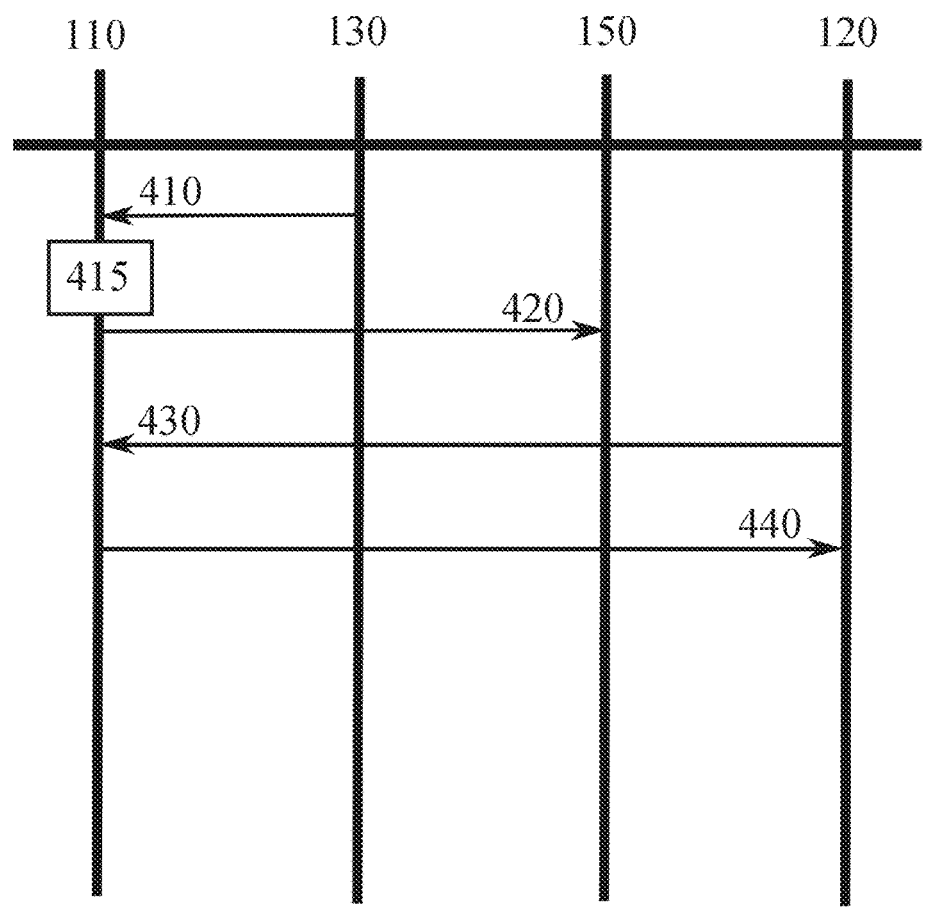
FIG. 4 is a signalling diagram illustrating signalling according to at least some embodiments of the invention.

FIG. 4 is a signalling diagram illustrating signalling according to at least some embodiments of the invention. On the vertical axes are illustrated, from left to right, computer 110, scanner 130, display 150 and device 120, using the reference numerals from FIG. 1.

In phase 410, computer 110 may receive from scanner 130 signals relating to a position of a device 120 relative to a head. The signals may comprise, for example, a video feed from which computer 110 may image-recognize homing aids 140. From knowledge of the physical layout of homing aids 140 disposed on the head and on device 120, computer 110 may determine the positions of the homing aids 140. The determined positions may be compared by computer 110 to positions of the homing aids 140 that would be associated with a position yielding a maximal induced electric field strength, to derive deviation information describing a deviation, in terms of at least one degree of freedom, of a position of device 120 from the position corresponding to the maximal induced electric field strength. The determining of the positions of the homing aids, and the derivation of deviation information, are illustrated as processing phase 415 in FIG. 4.

In phase 420, computer 110 may transmit, or cause to be transmitted, to display 150 indications of the deviation information derived in phase 415. For example, the indications transmitted in phase 420 may be comprised in a video signal from computer 110 to display 150. The indications may comprise a graphical guide signal, which may comprise at least one indicator such as, for example, at least one of the first, second, third, fourth, fifth and sixth indicator discussed above, to enable an operator of device 120 to reduce the amplitudes of the deviations.

Phases 410, 415 and 420 may take place in a continuous manner. In other words, computer 110 may receive signals from scanner 130 continuously and derive therefrom the deviation information, which may in turn be continuously transmitted, or caused to be transmitted, to display 150. This way, the operator may receive real-time or low-latency feedback to any movements he effects on device 120, making finding the position corresponding to the maximal induced electric field strength.

In optional phase 430, computer 110 may receive from device 120 a signal informing that device 120 is ready for use. Computer 110 may display an indication of readiness of device 120 in display 150.

In optional phase 440, computer 110 may transmit to device 120 a trigger signal to trigger device 120 to interact with the specific location. Computer 110 may transmit the trigger signal responsive to a determination, for example in phase 415, that device 120 is in a position where it can cause an electric field the strength of which exceeds a threshold strength to be induced in the specific location.

Phases 430 and 440 are optional independently of each other. In some embodiments, phase 430 and 440 are both absent. In other embodiments, they are both present. In yet further other embodiments, exactly one of phases 430 and 440 is present and the other is absent. Where phase 430 and 440 are both present, computer 110 may be configured to abstain from transmitting the trigger signal to device 120 in case device 120 has either not indicated it is ready, or has indicated it is not ready.

Figure 5:
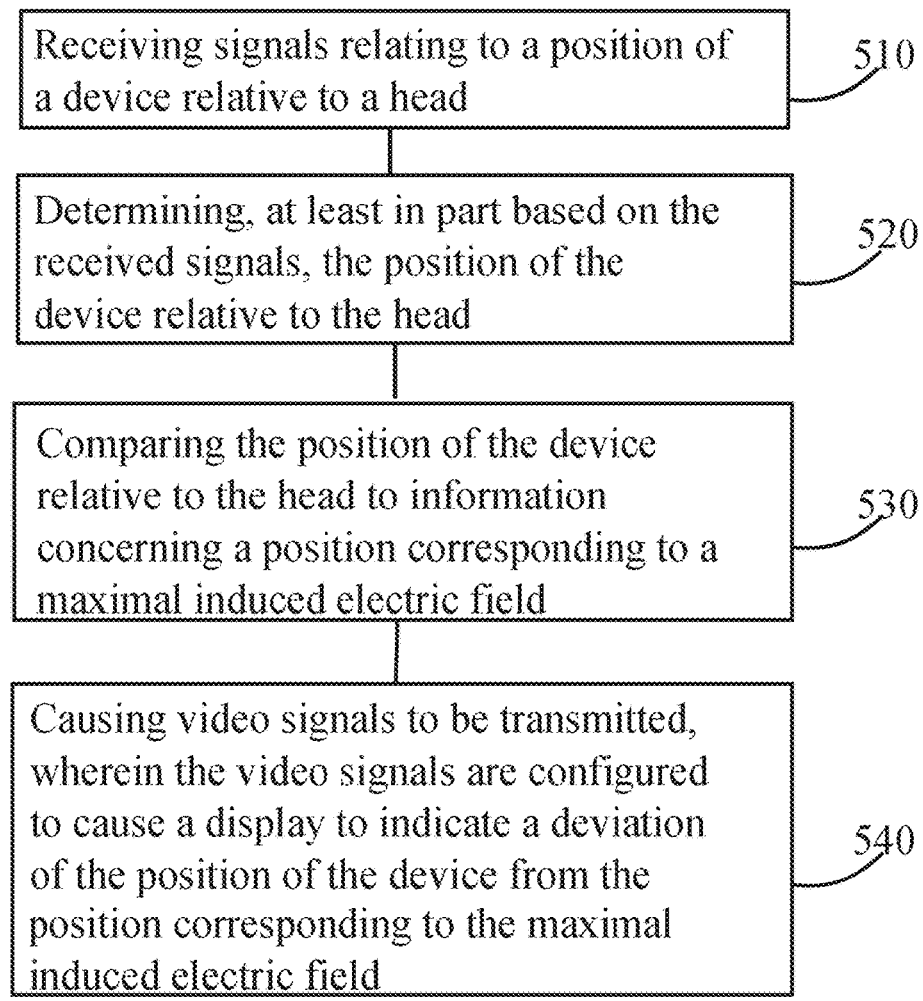
FIG. 5 is a flow graph of a method in accordance with at least some embodiments of the invention.

FIG. 5 is a flow graph of a method in accordance with at least some embodiments of the invention. The phases of the illustrated method may take place in computer 110, for example.

Phase 510 comprises receiving signals relating to a position of a device relative to a head. Phase 520 comprises determining, at least in part based on the received signals, the position of the device relative to the head. Phase 530 comprises comparing the position of the device relative to the head to information concerning a position corresponding to a maximal induced electric field. Finally, phase 540 comprises causing video signals to be transmitted, wherein the video signals are configured to cause a display to indicate a deviation of the position of the device from the position corresponding to the maximal induced electric field.

Figure 6:
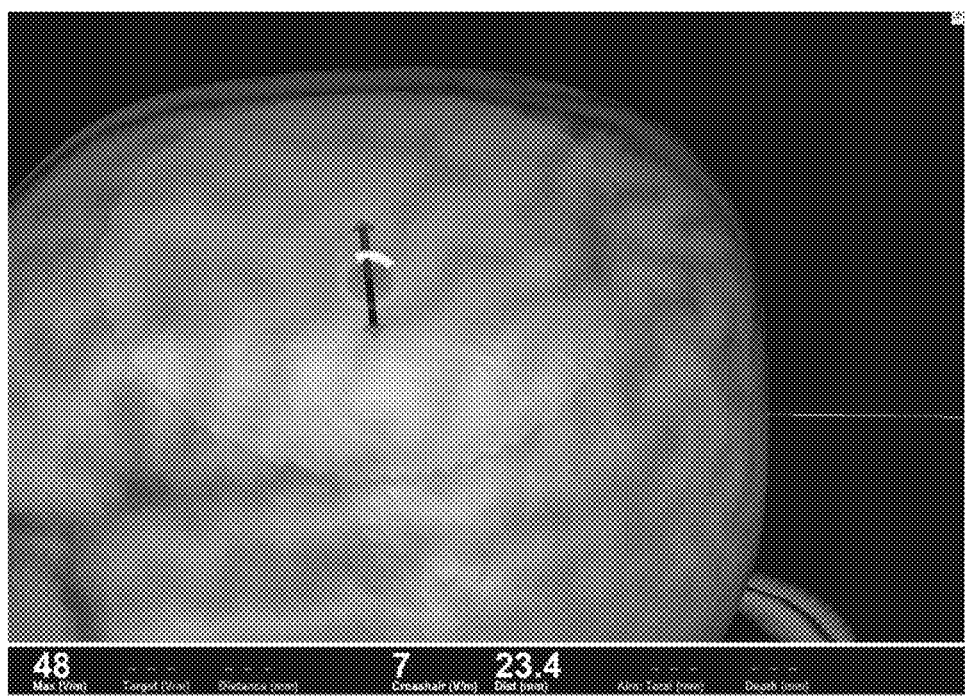
FIG. 6 is a first example view in accordance with at least some embodiments of the present invention.

FIG. 6 is a first example view in accordance with at least some embodiments of the present invention. FIG. 6 may be a view from display 150, for example. Illustrated is a standard brain with normal human brain anatomy in terms of ridges, which may or may not be anatomically exactly representative of the head being processed. An origin is displayed in a section of the screen signifying the location of an intended induced electric field, with an indication of deviation taking the form of a circle with one part highlighted. The circle may signify, for example, that device 120 needs to be rotated slightly clockwise in the yaw angle so as to maximize the electric field strength in the intended location.

Figure 7:
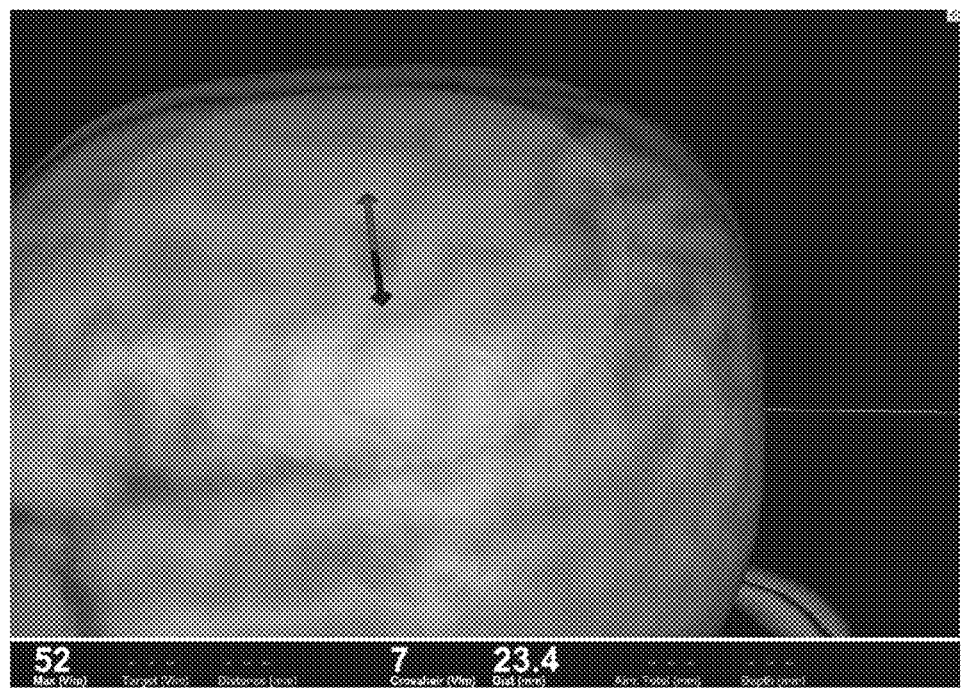
FIG. 7 is a second example view in accordance with at least some embodiments of the present invention.

FIG. 7 is a second example view in accordance with at least some embodiments of the present invention. The view of FIG. 7 may be from a same session as the image of FIG. 6. The circular indication of deviation is no longer present, signifying that the operator has successfully manoeuvred device 120 to align it to maximize the electric field strength, and device 120 is from that aspect ready to be triggered.

Figure 8:
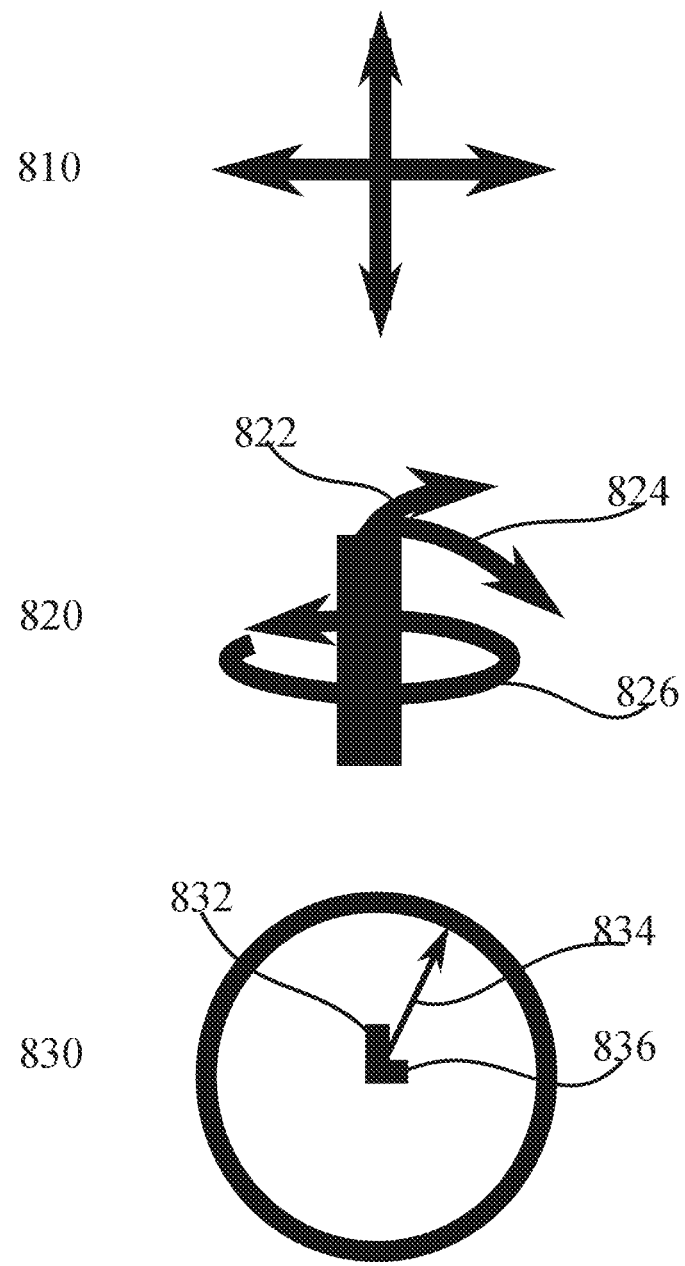
FIG. 8 illustrates example indicators in accordance with at least some embodiments of the present invention.

FIG. 8 illustrates example indicators 810, 820 and 830 in accordance with at least some embodiments of the present invention. The illustrated indicators are examples of indicators usable in indicating ways in which a device should be moved to eliminate a deviation, such as for example a deviation from a position where an induced electric field is highest.

Indicator 810 is a two-dimensional translational indicator, wherein the arrows may indicate deviations that relate to translational movement of a device along the surface of a head. The direction or directions of the arrow or arrows indicates a direction where the device should be moved to eliminate the deviation. In the illustrated indicator 810 four arrow components are shown for clarity, however in practice the user may see one or two arrows, indicating which direction or directions the device should be moved to eliminate or reduce the deviation.

Indicator 820 is a rotational indicator, where arrow 826 may indicate a deviation in terms of direction and/or amplitude of yaw deviation. Indicator 822 may indicate a deviation in terms of direction and/or amplitude of pitch deviation. Indicator 824 may indicate a deviation in terms of roll.

Indicator 830 is a rotational indicator, where arrow 834 may indicate a deviation in terms of yaw. Indicator 832 may indicate a deviation in terms of pitch, and finally, indicator 836 may indicate a deviation in terms of roll.

The indicators of FIG. 8 are examples only, to which the scope of the present invention is not limited.

In general there is provided an apparatus comprising at least one receiver configured to receive signals relating to a position of a device relative to a head. The signals may be received from scanner 130, for example. The apparatus may comprise at least one processing core configured to determine, at least in part based on the received signals, the position of the device relative to the head, to compare the position of the device relative to the head to information concerning a position corresponding to a maximal induced electric field, and to cause signals to be transmitted, and wherein the transmitted signals are configured to cause a display to indicate a deviation of the position of the device from the position corresponding to the maximal induced electric field. The deviation may comprise a deviation of a position of the device from a position where the device would cause a maximal electric field to be induced, without changing a location where the electric field would be induced. The apparatus may be configured to receive an instruction, the instruction instructing the apparatus to store the location where the electric field, or the maximum of the electric field, would be induced from a current position of the device. The apparatus may be configured to subsequently derive the deviation as a deviation between a current position of the apparatus and a position from where the device would induce a maximal electric field to the stored location.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. An apparatus comprising:
    at least one receiver configured to receive signals relating to a place and orientation of a device relative to a head, the device being capable of inducing an electric field in the head, a location in the head where the electric field is induced depending on a place where the device is, the strength of the electric field in the location depending on the orientation of the device;
    at least one processing core configured to determine, at least in part based on the received signals, the place and orientation of the device relative to the head, to compare the place and orientation of the device relative to the head to information concerning a place and orientation of the device corresponding to a maximal induced electric field strength being induced in a treatment area, and to cause signals to be transmitted, and
    wherein the at least one processing core is configured to firstly cause signals to be transmitted which are configured to cause a display to indicate a first deviation, of the place of the device from the place corresponding to the maximal induced electric field strength being induced in the treatment area, and then, upon the at least one processing core receiving signals that indicate the device is placed in the place corresponding to the maximal induced electric field strength being induced in the treatment area, the at least one processing core is responsively secondly configured to cause signals to be transmitted which are configured to indicate a second deviation, the second deviation being a deviation of orientation, such that changing the orientation of the device to eliminate the second deviation increases the induced electric field strength in the treatment area but does not change a specific location inside the head where the induced electric field strength is maximized.

2. An apparatus according to claim 1, wherein the transmitted signals are configured to cause the display to indicate the first deviation and the second deviation in terms of at least one of pitch, roll, yaw, rotation and distance.

3. An apparatus according to claim 2, wherein the transmitted signals are configured to cause the display to indicate the first deviation and the second deviation in terms of at least two of pitch, roll, yaw, rotation and distance.

4. An apparatus according to claim 2, wherein the transmitted signals are configured to cause the display to indicate the first deviation and the second deviation in terms of at least three of pitch, roll, yaw, rotation and distance.

5. An apparatus according to claim 2, wherein the transmitted signals are configured to cause the display to indicate the first deviation and the second deviation in terms of pitch, roll, yaw, rotation and distance.

6. An apparatus according to claim 1, wherein the apparatus is configured to cause the display to display a signal responsive to a determination that the device is at the place and orientation corresponding to the maximal induced electric field.

7. An apparatus according to claim 1, wherein the apparatus is configured to trigger the device responsive to a determination that the device is at the place and orientation corresponding to the maximal induced electric field.

8. An apparatus according to claim 1, wherein the at least one receiver is further configured to receive, from the device, at least one signal indicating whether the device is ready for use.

9. An apparatus according to claim 1, wherein the apparatus comprises the device, the device comprising a transcranial magnetic stimulation device.

10. An apparatus according to claim 1, wherein the apparatus is configured to, responsive to an instruction from a user, store a current specific location in the brain the device would interact with and subsequently determine the first deviation as a deviation between a current place of the device from where the device would induce a maximal electric field strength to the stored location.

11. An apparatus according to claim 1, wherein the place and orientation corresponding to the maximal induced electric field comprises a place and orientation corresponding to the maximal induced electric field at a specific location.

12. The apparatus according to claim 1 wherein the transmitted signals are configured to cause a graphical indication of the first and second deviations.

13. A method comprising:
    receiving signals relating to a position of a device relative to a place and orientation of the device relative to a head, the device being capable of inducing an electric field in the head, a location in the head where the electric field is induced depending on a place where the device is, the strength of the electric field in the location depending on the orientation of the device;
    determining, at least in part based on the received signals, the place and orientation of the device relative to the head, comparing the place and orientation of the device relative to the head to information concerning a place and orientation of the device corresponding to a maximal induced electric field strength being induced in a treatment area, and
    transmitting firstly first signals configured to cause a display to indicate a first deviation, of the place of the device from the place corresponding to the maximal induced electric field strength being induced in the treatment area, and upon the received signals indicating that the device is placed in the place corresponding to the maximal induced electric field strength being induced in the treatment area,
    responsively secondly transmitting second signals configured to indicate a second deviation, the second deviation being a deviation of orientation, such that changing the orientation of the device to eliminate the second deviation increases the induced electric field strength in the treatment area but does not change a specific location inside the head where the induced electric field strength is maximized.

14. A method according to claim 13, wherein the transmitted signals are configured to cause the display to indicate the first deviation and the second deviation in terms of at least one of pitch, roll, yaw, rotation and distance.

15. A method according to claim 13, wherein the transmitted signals are configured to cause the display to indicate the first deviation and the second deviation in terms of at least two of pitch, roll, yaw, rotation and distance.

16. A method according to claim 13, wherein the transmitted signals are configured to cause the display to indicate the first deviation and the second deviation in terms of at least three of pitch, roll, yaw, rotation and distance.

17. A method according to claim 13, wherein the transmitted signals are configured to cause the display to indicate the first deviation and the second deviation in terms of pitch, roll, yaw, rotation and distance.

18. A method according to claim 13, further comprising, responsive to an instruction from a user, storing a current specific location in the brain the device would interact with and subsequently determining the first deviation as a deviation between a current place and orientation and a place and orientation from where the device would induce a maximal electric field strength to the stored location.

19. A non-transitory computer readable medium having stored thereon a set of computer readable instructions that, when executed by at least one processor, cause an apparatus at least to:

receive signals relating to a position of a device relative to a place and orientation of the device relative to a head, the device being capable of inducing an electric field in the head, a location in the head where the electric field is induced depending on a place where the device is, the strength of the electric field in the location depending on the orientation of the device, determine, at least in part based on the received signals, the place and orientation of the device relative to the head, compare the place and orientation of the device relative to the head to information concerning a place and orientation of the device corresponding to a maximal induced electric field strength being induced in a treatment area, and transmit firstly first signals configured to cause a display to indicate a first deviation, of the place of the device from the place corresponding to the maximal induced electric field strength being induced in the treatment area, and upon the received signals indicating that the device is placed in the place corresponding to the maximal induced electric field strength being induced in the treatment area, responsively secondly transmit second signals configured to indicate a second deviation, the second deviation being a deviation of orientation, such that changing the orientation of the device to eliminate the second deviation increases the induced electric field strength in the treatment area but does not change a specific location inside the head where the induced electric field strength is maximized.

* * * * *